United States Patent [19]

Shillington

[11] Patent Number: 5,005,793
[45] Date of Patent: Apr. 9, 1991

[54] POLE CLIP NEEDLE CAP HOLDER

[75] Inventor: Richard A. Shillington, Leucadia, Calif.

[73] Assignee: Med-Safe Systems, Inc., Carlsbad, Calif.

[21] Appl. No.: 510,579

[22] Filed: Apr. 18, 1990

[51] Int. Cl.⁵ .................................... F16M 13/00
[52] U.S. Cl. ................................ 248/229; 248/230; 248/912
[58] Field of Search ............... 248/74.1, 911, 912, 248/229, 230, 74.2, 73, 75; 211/60.1; 128/DIG. 26; 604/93

[56] References Cited

U.S. PATENT DOCUMENTS

| | | | |
|---|---|---|---|
| 1,858,146 | 5/1932 | Ferguson | 248/75 X |
| 2,322,753 | 6/1943 | Thomas | 248/229 X |
| 3,263,820 | 8/1966 | McFadden et al. | 211/60.1 |
| 3,778,537 | 12/1973 | Miller | 248/229 X |
| 3,980,264 | 9/1976 | Tomasik | 248/912 X |
| 4,440,370 | 4/1984 | Rood | 248/75 |
| 4,654,026 | 3/1987 | Underwood | 128/DIG. 26 X |
| 4,832,294 | 5/1989 | Eidem | 248/229 X |

FOREIGN PATENT DOCUMENTS 2143425 2/1985 United Kingdom .................. 248/51

Primary Examiner—David L. Talbott
Attorney, Agent, or Firm—Baker, Maxham, Jester & Meador

[57] ABSTRACT

A needle cap holder for holding a cap in a stationary position for a needle to be reinserted therein, comprises a base member for attachment to a support surface, an arm having an inner end and an outer end and attached to the base at the inner end, and a needle cap holding member on the outer end of the arm having a plurality of vertical throughbores for holding a plurality of needle caps in an inverted stationary position for enabling the insertion of a needle therein.

15 Claims, 2 Drawing Sheets

POLE CLIP NEEDLE CAP HOLDER

BACKGROUND OF THE INVENTION

The present invention relates to needle cap holders and pertains particularly to an improved needle cap holder for IV needles and the like.

Accidental needle puncture frequently occurs when a nurse or physician attempts to recap a needle after giving an injection or drawing blood from a patient. Needle stick injuries may transmit such infectious particles as hepatitis B virus, non-A and non-B hepatitis virus, and human immunodeficiency virus (HIV), with disastrous consequences.

Hypodermic needles, IV needles and the like are covered with a removable protective sheath or cap, which is removed just prior to use of the needle. These caps are saved and placed back on the needle when the needle is removed from the patient. Holders have been used in the past which attach to an IV pole and contain a cup or cavity for holding one or more of the caps. When, the cap is to be placed on a needle, the cap is grasped in one hand, and the needle held in the other and inserted in the cap. If the needle misses the cap, it can result in the hand holding the cap being stuck or pricked with the needle. It is desirable that some means be available for enabling caps to be replaced on needles without the danger of sticking or puncturing the hand.

I have developed a needle cap holder that holds the caps in an inverted stationary position, so that the needle can be inserted without danger of sticking a hand.

SUMMARY AND OBJECTS OF THE INVENTION

It is the primary object of the present invention to provide an improved needle cap holder that enables the cap to be replaced without being held in the hand.

In accordance with a primary aspect of the present invention, a needle cap holder includes a base member for attachment to a support surface, with arm means extending outward from the base, and supporting means for holding a plurality of needle caps in an inverted stationary position for enabling the insertion of a needle therein.

BRIEF DESCRIPTION OF THE DRAWING

The above and other objects and advantages of the present invention will become apparent from the following description when read in conjunction with the accompanying drawings wherein.

DETAILED DESCRIPTION OF A PREFERRED EMBODIMENT

Figure 1:
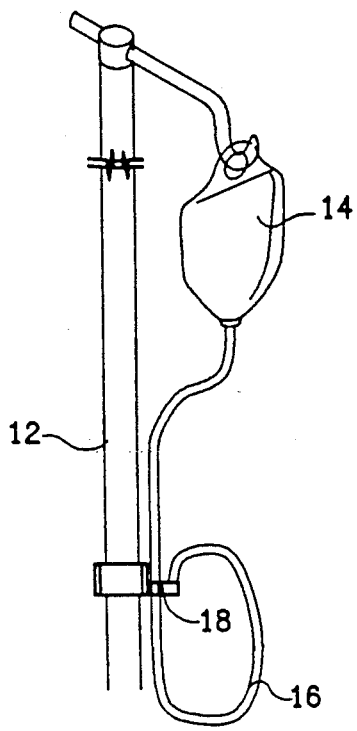
FIG. 1 is a perspective view illustrating a preferred embodiment of the invention in use.

Referring to FIG. 1 of the drawing, there is illustrated a typical intravenous injection system comprising a support pole 12, having suitable mounting means at the upper end on which is mounted an IV bag or bottle 14, from which an intravenous tube 16 extends with a needle (not shown) at the end thereof for the injection of a medicinal fluid into a patient. The needle (not shown) is supported by or in a cap holder 18 in accordance with the invention.

Figure 2:
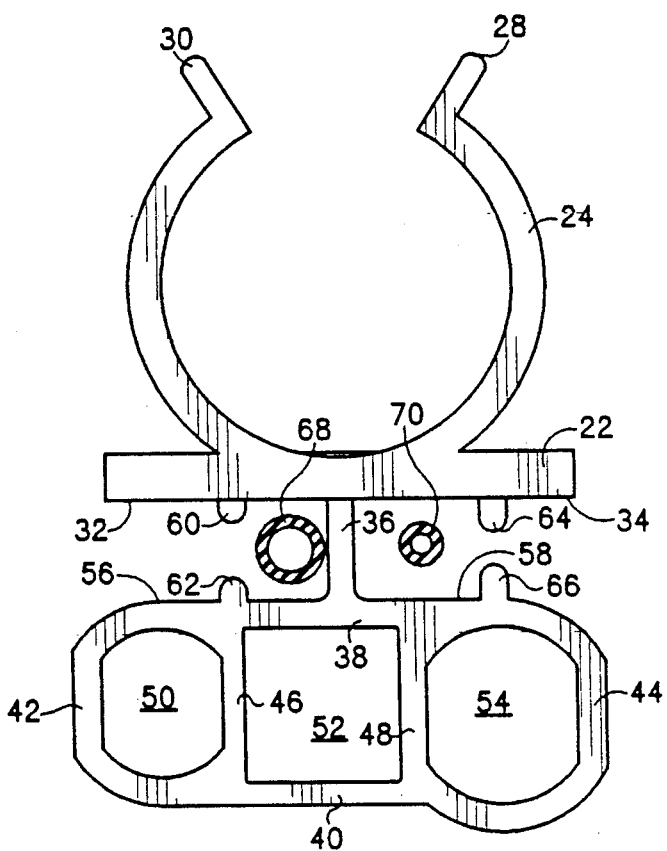
FIG. 2 is a top plan view of the embodiment of FIG. 1.
Figure 3:
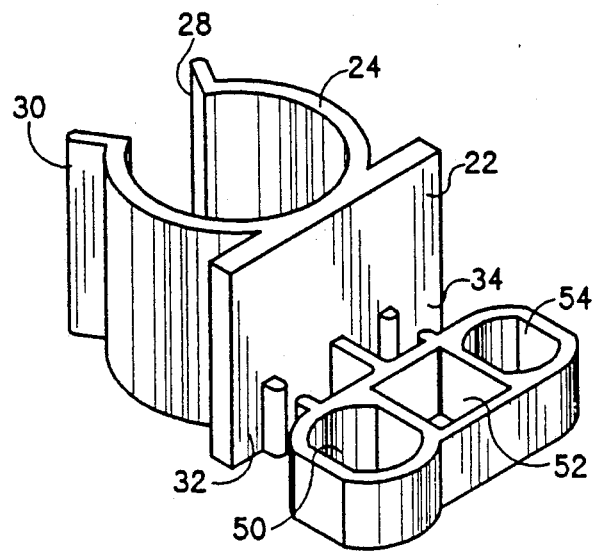
FIG. 3 is a perspective view of the embodiment of FIG. 2.

Referring to FIG. 2, the cap holder comprises a base or body member 22 having means, such as a pole clip of opposing arms 24 and 26 for attachment or mounting of the body member to an IV support pole. The clip comprises a pair of semi-circular opposed arms 24 and 26, which extend partially around and are biased into engagement with an IV pole for gripping or clamping attachment to the pole. Tabs 28 and 30 at the outer ends of the clamp arms 24 and 26 provide means for engagement by the fingers for forcing the clamp open for removal from a pole.

The base member 22 comprises essentially an elongated rectangular bar extending transverse to the axis of the clip, and forming vertical parallel faces 32 and 34 extending to opposite sides of an outwardly extending arm 36. The arm 36 is formed integral with the base 22, and extends outward from a center thereof for supporting a means for holding a plurality of needle caps in an inverted stationary position to enable the insertion of a needle therein. The needle support structure comprises a frame assembly having a plurality of vertical cap receiving bores. More specifically, it comprises a generally peripheral frame formed of an inner vertical wall 38 and an outer vertical wall 40, with end walls 42 and 44 forming the peripheral frame, with partitions 46 and 48 dividing the frame into a plurality of vertically oriented throughbores 50, 52 and 54. These throughbores are each defined by a continuous peripheral wall as shown in FIG. 2. The outer throughbores 50 and 54 are of a generally oval configuration, with parallel side walls and semi-circular end walls forming bores of different sizes for receiving caps of different sizes of essentially the same cross-sectional configuration. The center throughbore 52 is formed of four side walls defining a generally square configuration for receiving and supporting caps of a different configuration from those supportable in the other two holes or bores. More specifically, this bore receives caps of a square configuration. The needle caps have an elongated tubular main portion extending over the needle, with a closed end that covers the tip, and a flared open end that extends over and frictionally engages the needle hub for retaining it in place. The flared open end engages the top of the support to prevent the cover from slipping down through the bore.

The inner wall 38 of the peripheral frame forms a pair of vertical faces 56 and 58, which are parallel to and in opposition to faces 32 and 34 of the base member 22. These form outwardly extending vertical slots to either side of the arm 36, and in which are formed opposing ribs 60 and 62 on one side of the arm, and ribs 64 and 66 on the opposite side of the arm. These form semi-enclosures defining or forming tube retainers for retaining one or more tubes 68 and 70 therein against and close to the support pole. The ribs extend outward and define a spacing or opening therebetween that is slightly less than the diameter of the respective tubes 68 and 70. The tubes must be slightly compressed to pass into the retainer area where they are allowed to expand and become again unrestricted. This essentially clips or retains the tubes close into the IV pole, and thus helps prevent them becoming entangled or the like.

Figure 4:
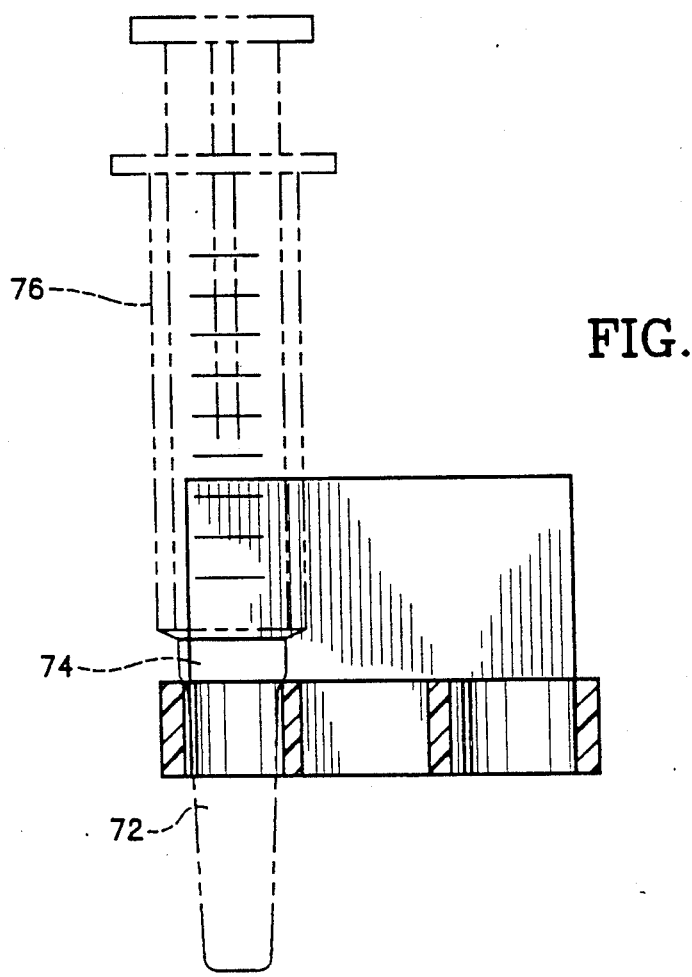
FIG. 4 is a front elevation view in section of the embodiment of FIG. 2.

Referring to FIG. 4, a typical example of a needle cap 72 is illustrated being supported in the bore 50. The cap 72 is engaged at a flared upper end 74, and held vertically in a stationary position to enable the insertion of a needle into the cap without the necessity of holding the cap in the hand. The needle may be on a syringe 76 (shown in phantom), or on an IV tube not shown. This reduces and essentially eliminates the chance of sticking or pricking the hand with the needle while attempting to install a protective cap. The other two bores 52 and 54 are designed to receive and mount caps of different sizes and configurations.

Figure 5:
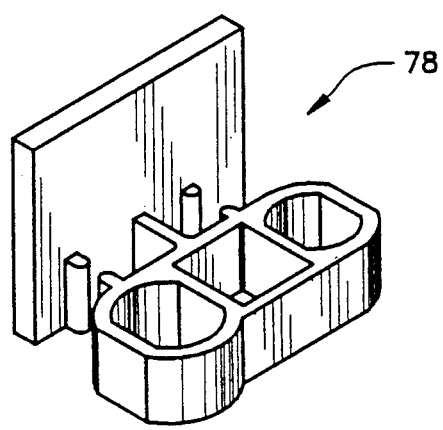
FIG. 5 is a perspective view of an alternate embodiment of the invention.

Referring to FIG. 5, there is illustrated an alternate embodiment of the invention, designated generally at 78, wherein the pole clips are eliminated. The holder has a base member 80 that is provided with a mounting surface that is substantially planar for bonding to a planar support surface. The bonding or mounting can be in any suitable form, such as by means of double adhesive tapes and adhesive material or by means of magnets or the like. Adhesives may be utilized where a permanent or semi-permanent mounting is desired to either a metallic or non-metallic surface. Permanent magnets may be utilized in the base of the mount when mounting to or on certain metal surfaces.

The cap holder is preferably a suitable plastic material having sufficient strength and durability to perform its function. Similarly, the material should have sufficient elasticity or springiness to enable the clip arms 24 and 26 to properly function in multiple instances.

In operation, a needle cap holder, as described, is selected and attached to a suitable supporting surface, such as to an IV pole or the like. Feeding tubes are clipped into the retainers and the needles caps when removed from the needles and are placed with the caps inverted in the appropriate ones of the cap holding bores 50, 52 and 54. When a needle is to be placed into a patient, the cap is removed therefrom and placed in the appropriate one of the throughbores in the inverted position. The cap is held stationary so that when the needle is removed from the patient it can be reinserted in the cap without the cap having to be held in the hand. This eliminates the danger of sticking the needle into a hand holding the cap.

While I have illustrated and described my invention by specific embodiments, it is to be understood that numerous changes and modifications may be made therein without departing from the spirit and scope of the invention as defined in the appended claims.

I claim:

1. A needle cap holder for holding a cap in a stationary position for a needle to be reinserted therein, comprising:
   a base member for attachment to a support surface;
   an arm having an inner end and an outer end and attached to said base at said inner end; and
   needle holding means on the outer end of said arm for holding a plurality of needle caps in an inverted stationary position for enabling the insertion of a needle therein, comprising a generally rectangular frame on the outer end of said arm and extending generally transverse thereto, first vertical throughbore defined by a continuous peripheral wall in said frame for axially receiving and holding a cap of a first size, and a second vertical throughbore defined by a continuous peripheral wall in said frame for axially receiving and holding a cap of a second size.

2. A needle cap holder according to claim 1 wherein:
   said base includes a semi-circular clip for partially encircling and clipping to a pole for support thereon.

3. A needle cap holder according to claim 1 wherein:
   one of said throughbores has a generally oval cross-sectional configuration.

4. A needle cap holder according to claim 1 wherein:
   one of said throughbores has a generally square cross-sectional configuration.

5. A needle cap holder according to claim 1 wherein:
   one of said throughbores has a generally oval cross-sectional configuration; and
   another of said throughbores has a generally square cross-sectional configuration.

6. A needle cap holder according to claim 1 wherein:
   said base and said frame define opposed generally parallel vertical surfaces at each side of said arm, and opposed vertical ribs on said surfaces spaced outwardly from said arm for retaining tubes therein.

7. A needle cap holder according to claim 6 wherein:
   said frame includes a third throughbore for holding a needle cap of a different configuration.

8. A needle cap holder according to claim 7 wherein:
   two of said throughbores have a generally oval cross-sectional configuration; and
   the other of said throughbores has a generally square cross-sectional configuration and is disposed between said two of said throughbores.

9. A needle cap holder for holding a cap in a stationary position for a needle to be reinserted therein, comprising:
   a base member having means for attachment to a support structure;
   an arm having an inner end attached to said base and an outer end for supporting cap holding means; and
   cap holding means comprising peripheral frame means having a plurality of vertical throughbores on the outer end of said arm for holding a plurality of needle caps in an inverted stationary position for enabling the insertion of a needle therein, wherein said base and said frame define opposed generally parallel vertical surfaces at each side of said arm, and opposed vertical ribs on said surfaces spaced outwardly from said arm for defining a partially enclosed area for retaining tubes therein.

10. A needle cap holder according to claim 9 wherein:
    said base includes a semi-circular clip for partially encircling and clipping to a pole for support thereon.

11. A needle cap holder according to claim 10 wherein:
    two of said throughbores have a generally oval cross-sectional configuration; and
    the other of said throughbores has a generally square cross-sectional configuration and is disposed between said two of said throughbores.

12. A needle cap holder according to claim 9 wherein: bonding to a planar surface for support thereon.

13. A needle cap holder for holding a cap in a stationary position for a needle to be reinserted therein, comprising:
    a base member having semi-circular means for attachment to a support structure;

an arm having an inner end attached to said base and an outer end for supporting cap holding means; and multiple needle cap holding means comprising peripheral frame means having a plurality of vertical needle cap receiving throughbores of different sizes on the outer end of said arm for receiving and holding a plurality of needle caps in an inverted stationary position for enabling the insertion of a needle therein, said base and said frame define opposed generally parallel vertical surfaces at each side of said arm, and opposed vertical ribs on said surfaces spaced outwardly from said arm for defining a partially enclosed tube retaining area for receiving and retaining tubes therein.

14. A needle cap holder according to claim 13 wherein:

said semi-circular means comprises clip for partially encircling and clipping to a pole for support thereon.

15. A needle cap holder according to claim 14 wherein:

two of said throughbores have a pair of opposed generally parallel side walls and semi-circular end walls; and the other of said throughbores has a generally square cross-sectional configuration and is disposed between said two of said throughbores.

* * * * *